(12) United States Patent
White et al.

(10) Patent No.: US 7,269,462 B2
(45) Date of Patent: Sep. 11, 2007

(54) MEDICAL ELECTRODES WITH LONG STORAGE LIFE

(75) Inventors: Sheldon S. White, Brookline, MA (US); Michael R. Dupelle, N. Attleboro, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 519 days.

(21) Appl. No.: 10/608,999

(22) Filed: Jun. 27, 2003

(65) Prior Publication Data

US 2004/0059405 A1  Mar. 25, 2004

Related U.S. Application Data

(63) Continuation-in-part of application No. 10/067,475, filed on Feb. 4, 2002, now abandoned.

(51) Int. Cl.
*A61N 1/04* (2006.01)
(52) U.S. Cl. ...................... 607/153; 600/397
(58) Field of Classification Search .......... 607/153
See application file for complete search history.

(56) References Cited

U.S. PATENT DOCUMENTS

| 4,002,239 | A | | 1/1977 | Buchalter |
| 4,058,127 | A | | 11/1977 | Buchalter |
| 4,526,176 | A | | 7/1985 | Bremer et al. |
| 4,543,958 | A | * | 10/1985 | Cartmell ..................... 600/391 |
| 4,729,377 | A | | 3/1988 | Granek et al. |
| 4,928,690 | A | | 5/1990 | Heilman et al. |
| 5,078,134 | A | | 1/1992 | Heilman et al. |
| 5,310,404 | A | * | 5/1994 | Gyory et al. ................. 604/20 |
| 5,622,168 | A | | 4/1997 | Keusch et al. |
| 6,477,411 | B1 | * | 11/2002 | Beck ........................... 604/20 |
| 6,526,303 | B1 | | 2/2003 | Scampini |

FOREIGN PATENT DOCUMENTS

WO          00/45698        8/2000

* cited by examiner

*Primary Examiner*—Kristen Mullen
(74) *Attorney, Agent, or Firm*—Fish & Richardson P.C.

(57) ABSTRACT

Medical electrodes are provided for use in applications that require long shelf life and/or shelf life at high temperatures. Some electrodes include high temperature adhesives and/or foams and an encapsulated electrolyte.

6 Claims, 7 Drawing Sheets

MEDICAL ELECTRODES WITH LONG STORAGE LIFE

CROSS-REFERENCE TO RELATED APPLICATIONS

This application is a continuation-in-part application of and claims priority to U.S. application Ser. No. 10/067,475, filed on Feb. 4, 2002 now abandoned.

TECHNICAL FIELD

The invention relates to medical electrodes, e.g., electrodes for use with external defibrillators.

BACKGROUND

Medical electrodes for use in procedures such as defibrillation typically include a conductor formed of metal, or formed of a conductive ink printed on a substrate, and a liquid or solid electrically conductive gel covering the conductor. The electrolyte is used to provide coupling between the conductor and the patient's skin. These electrodes often also include a foam backing layer, to which the conductor is adhered. An adhesive layer is used to adhere the electrodes to a patient. Such electrodes can be rendered unusable during storage by corrosion of the conductor and/or evaporation or degradation of the electrolyte. If the electrode is unusable at the time that the a caregiver needs to defibrillate a patient, the patient's life can be jeopardized or lost due to delay in locating a usable electrode.

SUMMARY

Public access defibrillators (PADs) and other types of automated external defibrillators (AEDs) are designed to be used by lay caregivers and/or emergency workers such as EMTs and firefighters to resuscitate victims of cardiac distress. PADs and AEDs are thus often stored in public buildings and emergency vehicles. As AEDs gain widespread acceptance for use by the general public, they will most likely also be stored in areas where they will be accessible to individuals who are in danger of cardiac distress, e.g., in the trunk of a car. Other types of external defibrillators may also be stored in adverse environments.

Electrodes that are used with such defibrillators may be stored for long periods of time at elevated temperatures. For example, a defibrillator stored in a vehicle, e.g., the trunk of a police car or the storage area of a fire truck, in a hot climate may be subjected to temperatures of 100-120° F. for weeks or even months at a time. Temperatures in a vehicle trunk can even reach 200° F. or more under some conditions.

We have found that these temperatures typically damage the electrode, often rendering it inoperable. Damage occurs in several ways. First, heat tends to accelerate corrosion of the conductor. Heat also tends to cause deterioration of the adhesives that are used in conventional electrodes. Finally, conventional electrolyte gels generally include materials that decompose or dissociate at temperature above about 140° F., causing deterioration of the electrolyte during high temperature storage. (Such gels may also lose their flexibility or even solidify at low temperatures, limiting the usefulness of the electrode in cold climates.)

Thus, when the electrode is needed in an emergency, it may not be functional, endangering the life of the person needing resuscitation if an extra electrode is not readily available. While it is often recommended that electrodes be inspected and replaced at predetermined intervals, e.g., yearly, it is generally difficult for consumers to remember to do this. Moreover, if the electrodes are exposed to very high temperature between replacement intervals, the electrodes may be rendered useless before the next replacement is due. In institutional settings, such as airports, it is more likely that electrodes will be regularly replaced, but doing so is costly and represents a significant cost in locations that require a number of defibrillators.

The present invention features electrodes that exhibit excellent shelf life at both high and low storage temperatures, i.e., the electrodes can be stored for extended periods at elevated or reduced temperatures without significant deterioration or loss of functionality. Thus, for example, the electrodes can be used after storage in vehicles kept outdoors at extreme temperatures without risk that the electrodes will be inoperative when needed.

In one aspect, the invention features a medical electrode including a housing; a conductor and an electrolyte disposed within the housing; and a high temperature adhesive that remains capable of adhering the electrode to a patient's skin after the adhesive has been exposed to temperatures of up to 200° F. for 4 hours, positioned to adhere a surface of the electrode to a patient's skin.

Some implementations of this aspect of the invention include one or more of the following features. The housing comprises a molded elastomeric member. The electrode further includes a high temperature adhesive positioned to secure components of the electrode to each other. The electrolyte is encapsulated. The high temperature adhesive is selected from the group consisting of high performance silicone or acrylic adhesives. The high temperature adhesive includes a high performance silicone transfer adhesive. The electrolyte is disposed in breakable capsules. The conductor includes a metal screen positioned between the capsules and the surface that is adhered to the patient. The electrode includes a foam backing that is joined to the conductor by a high temperature adhesive.

In another aspect, the invention features a medical electrode constructed to be applied to a patient's skin, the electrode including: (a) a housing; (b) a conductor within the housing; and (c) an electrolyte disposed within a chamber that is constructed to separate the electrolyte from the conductor until the electrode is to be used; the electrode being constructed so that the electrolyte, when released from the chamber, flows freely from the chamber towards the patient's skin without application of pressure to the chamber.

The invention also features a medical electrode constructed to be applied to a patient's skin, including: (a) a housing; (b) a conductor within the housing; (c) an electrolyte disposed within a chamber that is constructed to separate the electrolyte from the conductor until the electrode is to be used; and (d) an absorbent pad, positioned adjacent the conductor, on the side of the conductor that is closer to the patient's skin when the electrode is in use, and configured to absorb the electrolyte when it is released from the chamber and provide a wet layer between the conductor and the patient's skin.

The invention further features a medical electrode constructed to be applied to a patient's skin, including: (a) a housing; (b) a conductor within the housing; and (c) an electrolyte disposed within a chamber that is constructed to separate the electrolyte from the conductor until the electrode is to be used, the chamber being formed of a brittle material that is breakable by the application of a force to the chamber.

Some implementations of these aspects of the invention may include one or more of the following features. The chamber material is selected from the group consisting of glass, ceramic, and bakelite plastics. The chamber material is brittle at room temperature. The chamber includes a glass ampule. The chamber is located in an element (e.g., a release liner) configured to be removed from the electrode after the electrolyte is released from the chamber and before the electrode is placed on the patient. The electrolyte is a saline solution. The absorbent pad includes an absorbent material selected from the group consisting of sponges, gauze, carbon fiber mat, cellulose, and natural and synthetic fibrous batts. The conductor includes a screen or mesh material. The housing includes an elastomeric member. An edge of the conductor is molded into a portion of the housing.

In a further aspect, the invention features a medical electrode product including (a) an electrode comprising: (i) a housing; (ii) a conductor within the housing; and (iii) an electrolyte disposed within a chamber that is constructed to separate the electrolyte from the conductor until the electrode is to be used; and (b) a package, in which said electrode is disposed prior to use, including an actuator device constructed to release said electrolyte from said chamber when the electrode is removed from the package.

Some implementations include one or more of the following features. The chamber includes a breakable capsule, e.g., a glass ampule. The package comprises substantially rigid walls and the actuator device brings the walls closer together in order to open the package, at which time the walls are brought together sufficiently to break the capsule. The walls are hinged and rotate about the hinge to break the capsule. The actuator includes rolls through which the electrode is pulled during removal from the package. The rolls are positioned to rupture the chamber during removal. The actuator comprises a gradually tapered throat that narrows to slightly less than a separation that will break the capsule as the electrode is drawn through the tapered throat to remove it from the package. The electrode further includes an absorbent pad, positioned adjacent the conductor on the side of the conductor that is closer to the patient's skin when the electrode is in use. The conductor includes a screen or mesh material.

In another aspect, the invention features a medical electrode constructed to be applied to a patient's skin, the electrode including: (a) a housing; (b) a conductor within the housing; (c) an electrolyte disposed within a chamber that is constructed to separate the electrolyte from the conductor until the electrode is to be used; and (d) an indicator constructed to provide an indication to the user of whether the electrolyte has been released from the chamber.

Some implementations include one or more of the following features. The indication is a visual and/or audible indication. The indication includes a color change. The indicator is a humidity or wetness indicator visible through a transparent window in the housing. The indicator includes a semiconductor chip configured to store information concerning the status of the electrolyte and provide this information to a defibrillator control box upon demand. The indicator is configured to detect the presence of moisture. The indicator is configured, upon detecting moisture, to send information via the chip to the defibrillator control box upon demand. The indicator comprises a humidity or wetness sensor connected by wires extending from the housing.

In yet another aspect, the invention features a medical electrode product constructed to be applied to a patient's skin, the product including: (a) an electrode comprising a housing and a conductor and an electrolyte disposed within the housing; and (b) a package, within which the electrode is stored until use, that is pressurized sufficiently to minimize electrolyte loss through evaporation. By "minimize", we mean that evaporation is sufficiently slow so that the electrode will contain sufficient electrolyte to perform its intended function throughout the storage life of the electrode, i.e., until the next replacement of the electrode is due. Preferably, the package is pressurized sufficiently so that evaporation is prevented.

The invention also features a medical electrode product including (a) an electrode comprising a housing and a conductor and an electrolyte disposed within the housing; and (b) a cover disposed over the electrolyte in sealing engagement, the cover defining a region adjacent the electrolyte that is pressurized sufficiently to minimize electrolyte loss through evaporation.

Preferably, the package or region is pressurized to a pressure that is at least 25% above the ambient pressure at the time of sealing.

In a further aspect, the invention features a coupling device for use with a defibrillator paddle. The coupling device includes: (a) a housing; (b) a conductor within the housing; (c) an electrolyte disposed within a chamber that is constructed to separate the electrolyte from the conductor until the electrode is to be used; and (d) a mounting device constructed to allow the coupling device to be removably mounted on the defibrillator paddle.

Some implementations include one or more of the following features. The mounting device includes a clip. The mounting device includes an adhesive. The coupling device is configured to provide a conductive path from the defibrillator paddle to a patient's skin. The chamber includes a breakable capsule, e.g., a glass ampule. The capsule is configured to be broken by applying pressure to the coupling device. The device further includes an absorbent pad, positioned adjacent to the conductor on the side of the conductor that is opposite the defibrillator paddle when the coupling device is in use. The conductor includes a screen or mesh material. The coupling device further includes a screen configured to prevent fragments of the capsules from contacting a patient's skin when the capsules are broken.

The invention also features a medical electrode constructed to be applied to a patient's skin, the electrode including: (a) an elastomeric housing, configured to conform to the body contours of the patient; (b) a conductor within the housing; and, (c) within the housing, an electrolyte disposed within a chamber that is constructed to separate the electrolyte from the conductor until the electrode is to be used.

Some implementations include one or more of the following features. The electrode further includes a high temperature adhesive that remains capable of adhering the electrode to a patient's skin after the adhesive has been exposed to temperatures of up to 200° F. for 4 hours, positioned to adhere a surface of the electrode to a patient's skin. The housing is a unitary, integrally molded part. The housing includes a thermoplastic elastomer.

Other features and advantages of the invention will be apparent from the detailed description and drawings, and from the claims.

DETAILED DESCRIPTION

Electrode Structure

Figure 1:
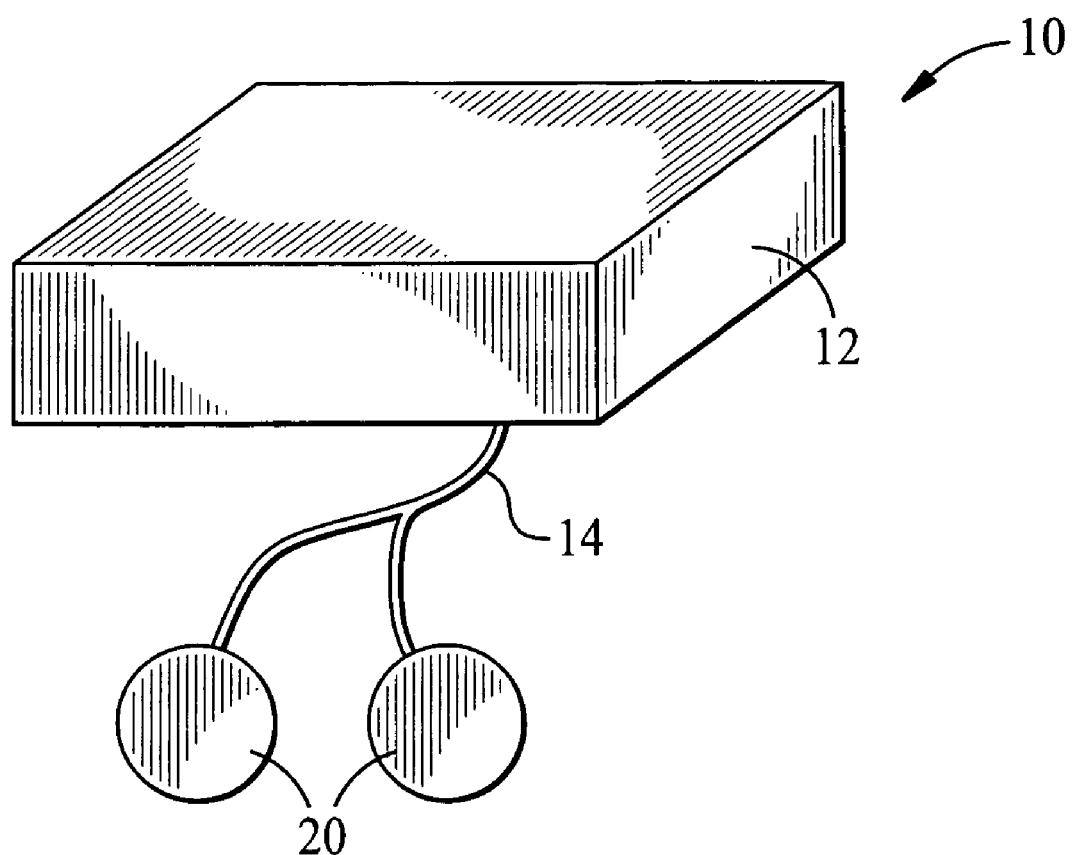
FIG. 1 is a schematic view of an external defibrillator.

Preferred electrodes are suitable for use with external defibrillators, including Automated External Defibrillators. As shown in FIG. 1, an external defibrillator 10 includes a defibrillator control box 12, a pair of electrodes 20, and a cable 14 connecting the electrodes to the control box. The electrodes are generally stored with the control box. When a patient is in need of resuscitation, a caregiver removes the electrodes and prepares them for use as will be discussed below. When the electrodes are ready for use, the caregiver adheres each electrode to the skin of the patient's chest. The caregiver may then be instructed by the control box to stand back and apply a defibrillating shock to the patient.

Figure 2:
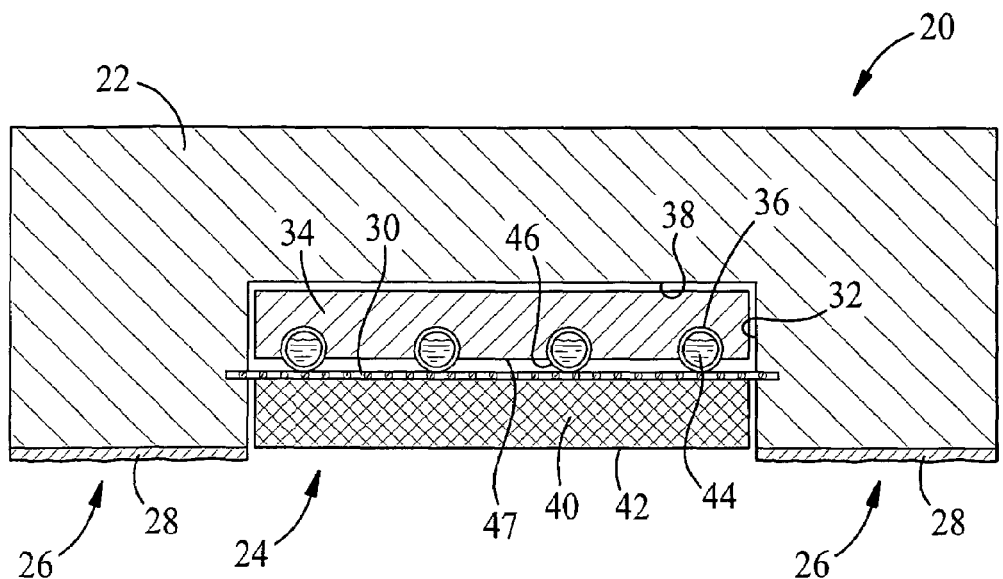
FIG. 2 is a cross-sectional view of an electrode according to one embodiment of the invention.

Referring to FIG. 2, electrode 20 includes a molded elastomeric housing 22 that defines a well 24 and a patient-contacting surface 26. A layer of pressure sensitive adhesive 28 is provided on surface 26, to enable the electrode 20 to be adhered to a patient's skin. The molded, one-piece construction of the housing is durable and is capable of withstanding extended storage at high temperatures. While the elastomeric housing 22 is shown as being relatively thick, it may be thinner if desired.

A conductive screen 30 is attached to the side wall 32 of well 24, e.g. by insert molding the screen into the housing. The conductive screen 30 functions as the conductor for the electrode. If desired, the screen 30 may be formed of a non-conductive material, e.g., plastic, and a separate conductor (not shown) may be included. If a separate conductor is used, the conductor generally should include holes, to allow passage of electrolyte through the conductor when the electrolyte is released, as will be discussed below.

An elastomeric block 34, containing four glass ampules 36, is positioned between the screen 30 and the upper wall 38 of well 24. (The number of ampules will vary, and is selected based on the size of the ampules and size of the electrode.) The glass ampules 36 contain an electrolyte 44. Until the electrode is to be used, the electrolyte remains sealed in the ampules, preventing the electrolyte from evaporating and eliminating corrosion of the conductor by the electrolyte during storage. Because the electrolyte is separated from the conductor in this manner, it is also not necessary to store the electrode in a hermetically sealed package. As long as the electrode is protected from impact during storage, as discussed below, release will not occur until the caregiver is ready to apply the electrode to a patient.

An absorbent pad 40 is positioned below the screen 30, with its exposed surface 42 generally aligned with the patient-contacting surface 26 of the housing. The absorbent pad is generally held in the electrode by adhering it to the pad or by insert molding it in place in the housing. Because the absorbent pad is positioned in well 24, there is a ring of elastomeric material around the absorbent to restrict flow of electrolyte away from the area defined by well 24. If the volume of electrolyte is balanced with the size and absorption properties of the absorbent pad, flow of electrolyte can be minimized, in which case the ring of elastomeric material may be eliminated.

When the electrode is to be used, the caregiver breaks the ampules, e.g., by removing the electrode from a package that is designed to break the ampules (as will be discussed below) or by the caregiver applying pressure to the electrode. The electrolyte is released as a result of an action performed by the caregiver and quickly saturates the absorbent pad, readying the electrode for use. The screen 30 catches the fragments of the broken ampules, preventing any contact of the fragments with the patient's skin.

Preferably, as shown, the ampules are molded into the elastomeric block 34 so that only a small radial portion 46 of each ampule extends beyond surface 47 of the elastomeric block. Portion 46 is sufficiently large so that, when the ampule is broken, the electrolyte can easily flow out of the ampule, but sufficiently small so that most of the glass remains embedded in the elastomeric block.

Figure 3:
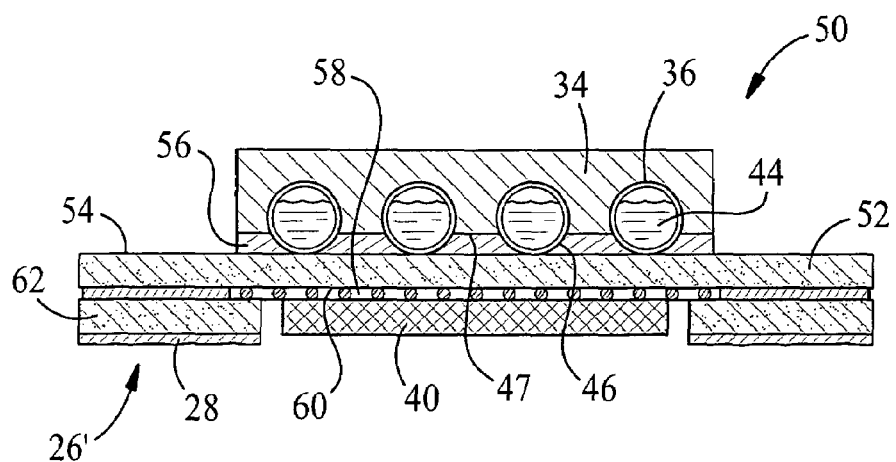
FIG. 3 is a cross-sectional view of an electrode according to an alternate embodiment of the invention.

FIG. 3 shows an electrode 50 according to an alternative embodiment, in which the molded elastomeric housing 22 is replaced by a foam backing 52. In this case, the elastomeric block 34 is adhered to a first surface 54 of the foam backing by an adhesive layer 56. Foam backing 54 includes open areas (not shown) through which liquid can flow from the ampules 36 to the absorbent pad 40. A conductor 58 is adhered to a second, opposite surface 60 of the foam backing. The conductor 58 is a screen or mesh, or includes apertures through which the liquid electrolyte can pass. As discussed above, an absorbent pad 40 is positioned below the conductor and is adhered thereto or otherwise secured to the electrode. A second layer 62 of foam is adhered to the foam backing 52 to define a well in which the absorbent 40 sits and to provide a patient-contacting surface 26' that carries pressure sensitive adhesive 28.

Figure 9:
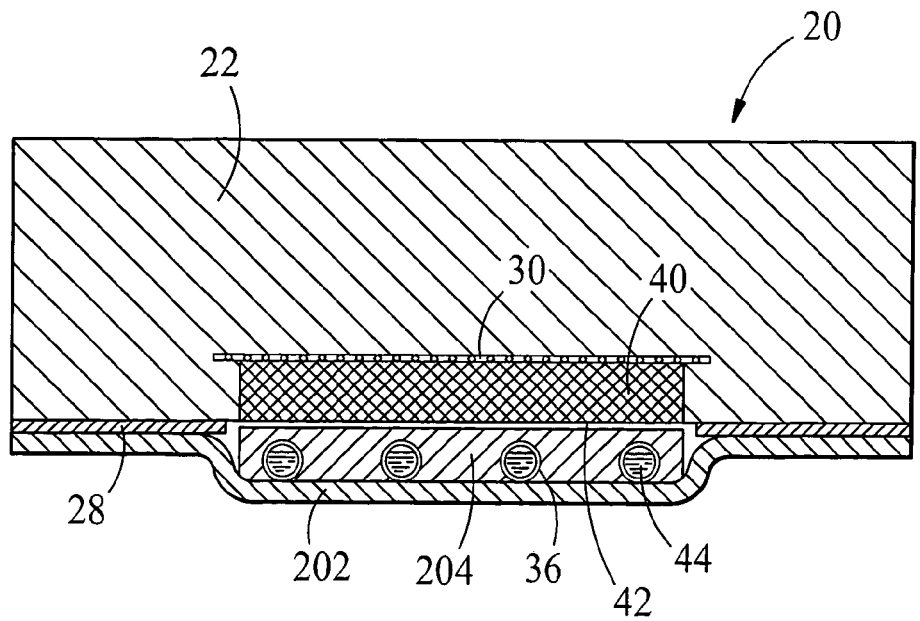
FIG. 9 is a cross-sectional view of an alternative electrode.

FIG. 9 shows another implementation, in which the ampules are located in the removable release liner portion of the electrode. Liner 202 is shaped to provide room for ampules 36 and molded elastomeric block 204 surrounding the ampules. After the ampules are broken to release the electrolyte, the liner 202 and block 204 (with the shards of the broken ampules still within the block) is removed from the electrode and discarded. The ampules may be broken in this implementation using any of the various techniques described herein.

Suitable Materials

The ampules may be commercially available pre-filled saline ampules. The glass of the ampules is preferably 0.005 to 0.010 inch thick, more preferably 0.006 to 0.007 inch thick. The ampules may have any desired dimensions that will fit in the available space, but are typically cylindrical, measuring about 2.5 to 3 inches in length and about 0.25 to 0.35 inch in diameter. The ampules should be breakable with relatively light pressure, and should be of a glass that will break into relatively large fragments. The glass of the ampules may be scored, to facilitate breakage at low applied pressures. Preferably, the ampules are not completely filled with electrolyte, so that there is sufficient headspace to allow for expansion of the electrolyte if it freezes and increased gas pressure of the electrolyte at elevated temperatures, preventing rupture of the ampule under these conditions. Other suitable brittle materials for the ampules include ceramics and brittle, high temperature resistant plastics such as high glass transition temperature or highly cross-linked plastics.

It is generally preferred that the electrolyte be a low viscosity conductive liquid, such as a saline solution. A low viscosity electrolyte will flow freely into the absorbent pad when the ampules are broken, without requiring excessive pressure to be applied to the electrode. Preferably, the electrolyte is selected to flow into the absorbent pad by gravity and/or capillary action, without the need for application of any pressure (pressure may be applied to the electrode if desired for other reasons, e.g., to adhere the electrode to a patient, but pressure is not necessary to achieve flow of the electrolyte to the patient's skin). Saline solutions are advantageous for use in electrodes that will be stored at high and/or low temperatures. Water may be used in the ampules instead of a saline solution, if the electrode will be stored and used above 0° C. If water is used, the absorbent pad may be impregnated with a salt if additional conductivity is desired.

The absorbent pad 40 has sufficiently high absorbency to prevent the electrolyte from flowing out of the electrode and being lost, but sufficiently low absorbency to allow the electrolyte to contact and wet the patient's skin. If desired, the absorbent material may be impregnated with a thickening agent, e.g., 2-acrylamido-2-methylpropane sulfonic acid (AMPS), to thicken or gel the low viscosity electrolyte and thereby control its flow properties. Suitable absorbent materials include sponges, gauze, carbon fiber mat, and absorbents suitable for use in diapers such as cellulose and natural and synthetic fibrous batts. The thickness of the absorbent pad will depend on the absorbency of the material used. Preferably the absorbent pad is configured (a) to provide a wet surface at the interface between the pad and the patient's skin, and a wet layer between the conductor and the interface between the pad and the patient's skin, while (b) minimizing flow of liquid from the electrode out over the patient's skin beyond the periphery of the electrode.

Screen 30 preferably has the smallest possible mesh size that will allow the particular electrolyte that is used to flow freely through the screen without the need for application of pressure to the electrode. Generally, for a saline solution, the mesh size is from about 300 to 500 openings per square inch. A suitable screen for use with a saline solution is an expanded metal mesh having diamond shaped openings with a mesh size of about 400 openings per square inch and a screen thickness of about 0.005 to 0.020 inch. Suitable mesh size will depend on the thickness of the screen, the viscosity of the electrolyte, temperature, and other factors. For example, if a more viscous electrolyte is used, a screen having a larger mesh size may be required.

If a conductive screen is used (rather than a non-conductive screen and a separate conductor) the screen is generally formed of a metal. Preferably, the conductive screen is an expanded metal or etched metal mesh, as a woven metal screen may produce some undesirable electrical noise due to relative movement of the strands. If a separate conductor is provided, the screen may be formed of plastic or any desired non-conductive material that can be fabricated into a screen or mesh. A porous fabric, e.g., cheesecloth, may be used; preferably the fabric is relatively non-absorbent.

Suitable elastomers for housing 22 and elastomeric block 34 include thermoplastic elastomers, e.g., block copolymers such as those available from Shell under the tradename KRATON rubbers. Suitable elastomers will have sufficient flexibility so that the molded housing 22 and elastomeric block 34 will flex and conform to body contours when the electrode is adhered to a patient. This is particularly important in relatively large defibrillation electrodes, which extend over a significant area of the patient's chest and thus generally need to bend to accommodate the curvature of a patient's chest and/or the patient's breast tissue. If the electrode does not adequately conform to body contours, sufficient electrical contact may not be achieved and defibrillation may be impossible or ineffective, endangering the patient's life.

If the electrode is expected to encounter high temperatures during storage the pressure sensitive adhesive 28 that is used to adhere the electrode to a patient should be high temperature stable, and should adhere well to the patient at the temperature that the electrode is likely to be at when it is used (generally ambient temperature or somewhat higher if the electrode has just been removed from a hot storage area). Preferably, the adhesive remains capable of adhering the electrode to a patient's skin after the adhesive has been exposed to temperatures of up to 200° F. for 4 hours or longer. Suitable high temperature contact or pressure sensitive adhesives include high performance silicone or acrylic adhesives. An example of a suitable high temperature adhesive is a transfer high performance silicone adhesive commercially available from Adhesives Research, Inc., Glen Rock, Pa., under the trade name ARclad® 7876. If the electrode will not be stored at high temperatures, a conventional pressure sensitive adhesive suitable for use in an electrode may be used. If an adhesive is used to hold layers of the electrode together, for example in the embodiment shown in FIG. 3, this adhesive should also be stable at high temperatures, and capable of holding the layers securely together. The high performance adhesives discussed above would be suitable for adhering the layers together.

Electrode Packaging

In order to protect the ampules from unintentional breakage, it is generally preferred that the electrode be stored in a relatively rigid, protective package. Suitable materials for the packaging include rigid plastics, metals, and other rigid and semi-rigid materials.

Figure 4:
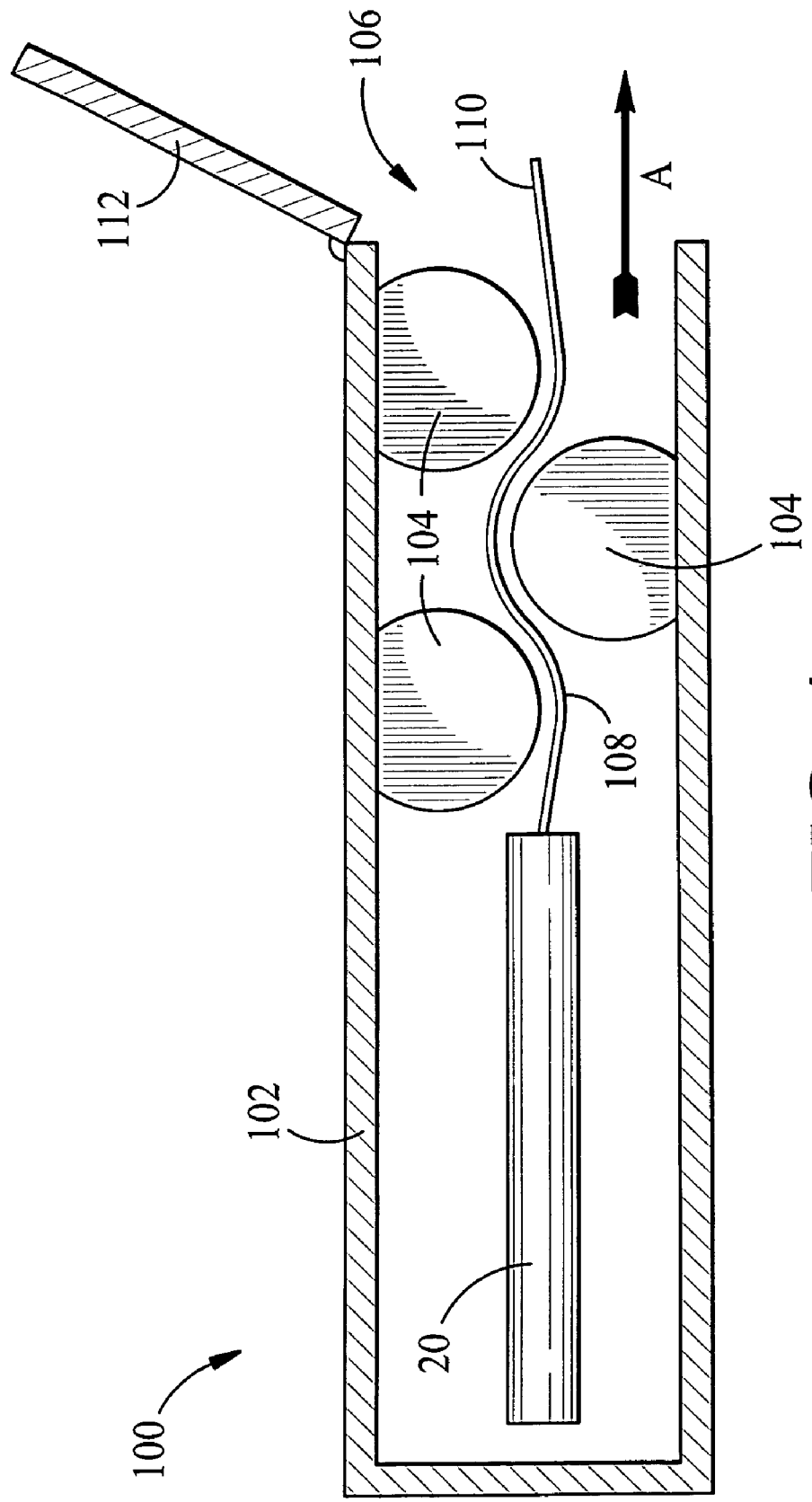
FIG. 4 is a schematic side view of a package containing an electrode, with the end of the packaged removed to expose the internal structure of the package.

If desired, the package may include an actuating device that will rupture the ampules as the electrode is being removed from the packaging. For example, as shown in FIG. 4 the package 100 may include a rigid box 102 in which are mounted a series of rolls 104. The rolls 104 define a tortuous path through which the electrode 20 must pass as it is pulled (arrow A) through the opening 106 of the box. A leader 108 extends from the electrode 20 to provide a tab 110 which may be pulled by the user to start the removal of the electrode 20 from the box. Prior to use, box 102 is sealed, e.g., by flap 112. As discussed above, it is not necessary to hermetically seal the box.

Other types of actuation devices may be used, or the ampules may be broken by the caregiver after removing the electrode from the package, e.g., by placing the electrode on the patient or a relatively firm surface and applying pressure to the top surface of the electrode.

Figure 10:
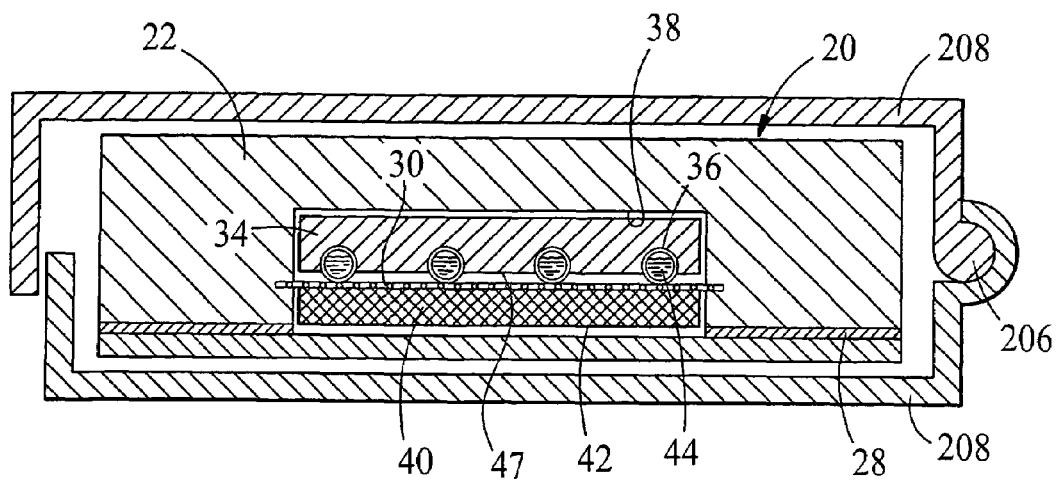
FIG. 10 is a cross-sectional view of a package containing an electrode.
Figure 11:
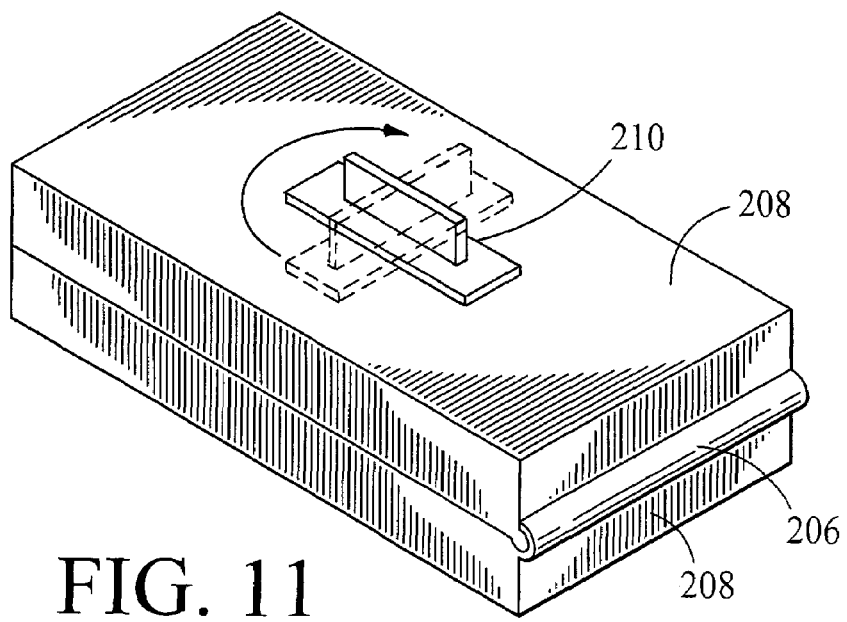
FIG. 11 is a perspective view of the exterior of the package of FIG. 10.

FIGS. 10-11 show one implementation of a substantially rigid plastic package for storing the electrode 20. The package includes upper and lower halves 208 hinged at one end 206. A cam mechanism (not shown) causes the two halves to move closer together when handle 210 is turned (as suggested by the arrow and dashed lines showing the turned position) to open the package. This movement causes ampules 36 to break and deliver electrolyte to the electrode. After the two halves complete this movement, they can be separated to permit the electrode to be removed. This results in the electrode being activated (by breakage of the ampules) when the package is opened but not before.

Figure 8:
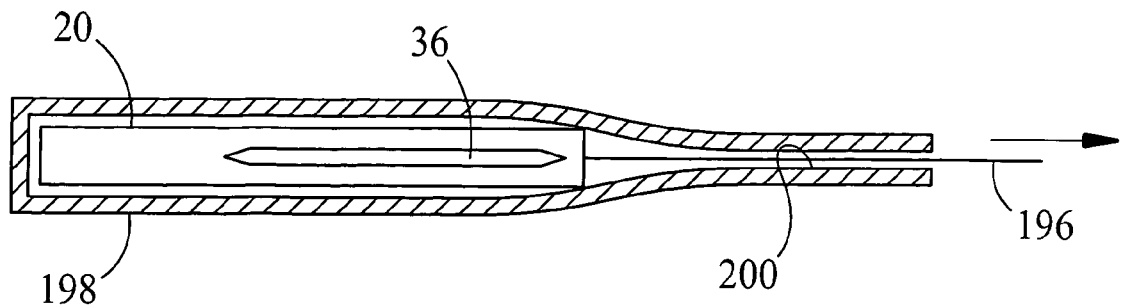
FIG. 8 is a cross-sectional view of a package containing an electrode.

FIG. 8 shows another implementation in which the electrode 20 is stored inside a substantially rigid enclosure 198, and is removed by pulling on tab 196. This causes the electrode to move through a gradually tapered throat 200, which is sized to be slightly smaller than what will cause the ampules 36 to break as the electrode is drawn through the throat.

Coupling Devices for Defibrillator Paddles

A structure similar to that described above with reference to FIG. 2 may be used to form a coupling device for use with a defibrillator paddle. Coupling devices are used to provide an electrolyte interface between the surface of the paddle and the skin of the patient.

Figure 5:
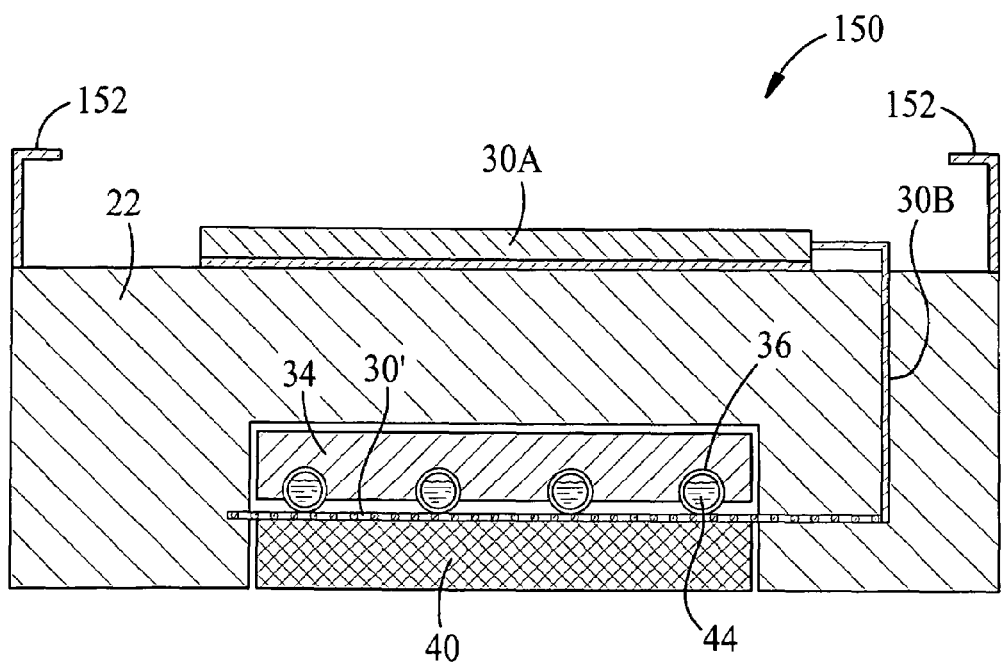
FIG. 5 is a cross-sectional view of a coupling device according to one embodiment of the invention. FIG. SA is a schematic view showing the coupling device in use on a defibrillator paddle.

A coupling device 150 is shown in FIG. 5. The structure of the coupling device is the same as that of the electrode 20 shown in FIG. 2, except that adhesive 28 is omitted (because the defibrillator is held in place on a patient rather than adhered to the patient), clips 152 are provided to secure the coupling device to the defibrillator paddle, and a lead 30B and conductive plate 30A are provided to establish a conductive path between conductor 30' and the defibrillator paddle 156.

Figure 5A:
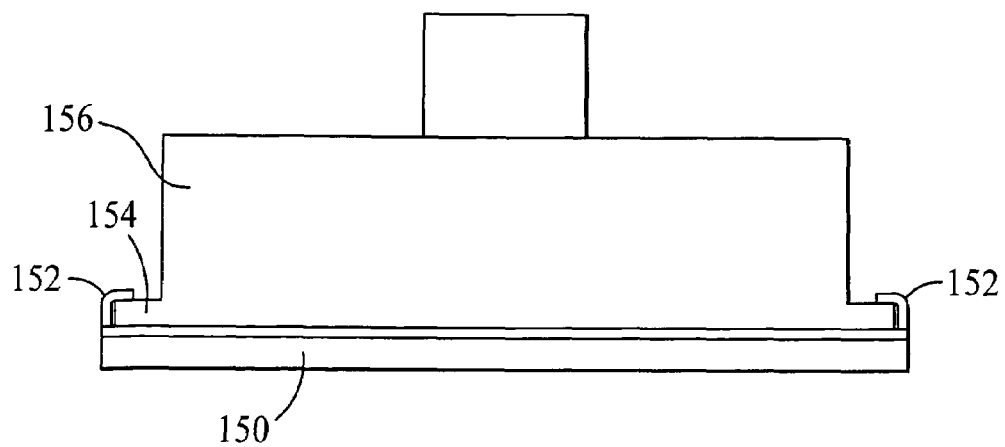

The coupling device 150 is shown in use in FIG. 5A. Clips 152 securely attach the coupling device 150 to shoulder 154 of defibrillator paddle 156.

To release the electrolyte from ampules 36, the caregiver may clap the defibrillator paddles together, with the coupling devices 150 in place, or may press the defibrillator paddles against the patient or a relatively firm surface.

Safety Features

If desired, the electrode or coupling device may include an indicator, to indicate to the caregiver whether the electrolyte has been accidentally released during storage, rendering the electrode ineffective. Without such an indicator, the caregiver may not realize that the electrolyte has been inadvertently released during storage, if the electrolyte has evaporated and the electrode is dry to the touch.

The indicator may include a color change element, e.g., an integrated circuit chip that changes color if conductivity is detected, or a color changing humidity or wetness indicator visible through a transparent window. Instead or in addition, the indicator may include an audio alarm, e.g., an audible signal emitted by the control box of the defibrillator. The alarm may be continuous from the time the accidental release occurs, or may be emitted only when the defibrillator detects that a caregiver may be activating the defibrillator, e.g., when the defibrillator cover is removed. The indicator may also include an electrical sensor connected to external electronics by wires extending from the electrode.

The electrode or coupling device would in either case include a test circuit that would read infinite resistance as long as the electrolyte remained encapsulated, and would detect current in the event of accidental electrolyte release.

If the electrode is pre-connected to a defibrillator, when current is detected a warning will be sent directly to the defibrillator. If the electrode is not pre-connected (or, optionally, as an additional safeguard if it is pre-connected) the electrode will include a semiconductor chip configured to send a signal to the defibrillator control box indicating the status of the electrode. In either case, the defibrillator will provide a visual and/or audible indication to the caregiver.

OTHER EMBODIMENTS

Other embodiments are within the scope of the following claims.

Figure 6:
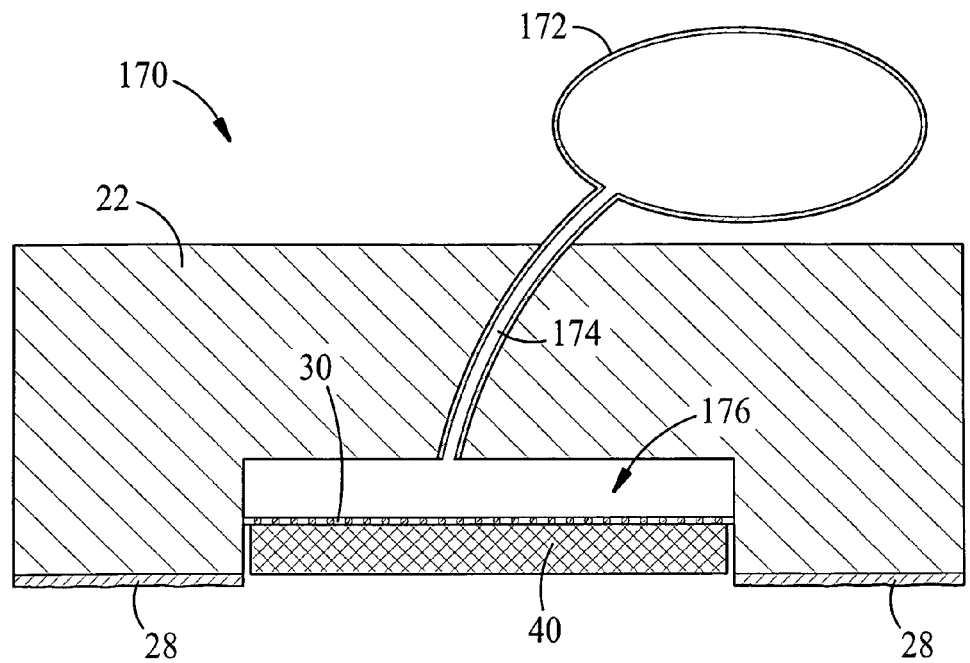
FIG. 6 is a cross-sectional view of an electrode according to another alternate embodiment on the invention.

For example, while glass ampules have been shown and described above, other techniques for encapsulating the electrolyte may be used. For example, as shown in FIG. 6, in an alternative electrode 170, the electrolyte can be encapsulated in an elastomeric reservoir 172. The reservoir 172 can be filled, during manufacturing, by creating a vacuum in the reservoir, e.g., by compressing the elastomeric reservoir to largely exclude air, and allowing the electrolyte to be drawn into the reservoir by the vacuum, e.g., by releasing the compression with an opening in the reservoir immersed in a supply of the electrolyte. Subsequent pressure applied to the reservoir 172 when the caregiver prepares the electrode for use will cause the electrolyte to be released from the reservoir and flow through a tube 174 to a sub-reservoir 176. The electrolyte then flows into the absorbent pad 40, as described above, and the electrode is ready to use.

Further, while low viscosity electrolytes, e.g., saline solution, have been described as preferred, a conventional electrolyte gel may be encapsulated if desired.

Also, while electrodes including encapsulated electrolyte have been described above and shown in the figures, the high temperature adhesives discussed above are also suitable for use in other types of electrodes including conventional electrodes in which the electrolyte is not encapsulated.

Figure 7:
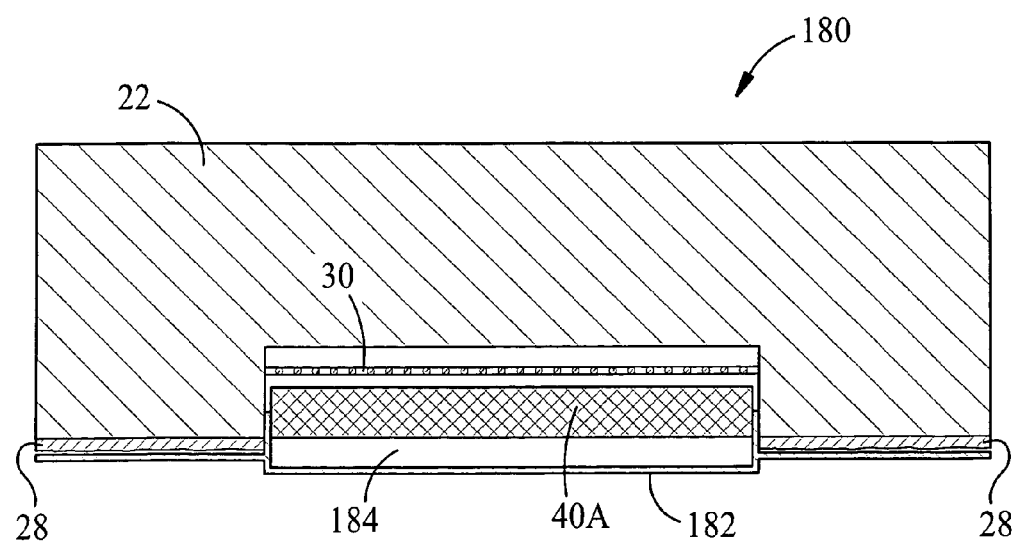
FIG. 7 is a cross-sectional view of an electrode according to another alternate embodiment of the invention.

Moreover, in an alternate embodiment (electrode 180, shown in FIG. 7), the electrolyte is not encapsulated, but is instead prevented from drying out by placing a pressurized cover 182 over the electrolyte. The package or cover is pressurized, for example, to a pressure that is approximately 25% higher than the ambient pressure at the time of assembly. In this embodiment, the electrolyte is typically an electrolyte gel, provided in a pre-gelled absorbent pad 40A. The area 184 under the cover 182 can be pressurized, for example, by including a check valve (not shown) in the cover 182 and pressurizing area 184 through the check valve.

Additionally, while single electrodes are discussed above, the electrode structures disclosed are suitable for use in electrode assemblies, in which a pair of electrodes are mounted on a single, integral backing for ease of application to a patient.

An annular ring of absorbent material could surround the active skin-contacting area of the electrode, e.g., around the absorbent pad 40. The ring of absorbent material would serve to absorb any excess saline solution that might otherwise be forced into the ring of pressure sensitive adhesive 28, causing the adhesive to fail, and allowing saline to leak through the adhesive onto the exposed skin of the patient (e.g., if the patient were lying on his side with the electrode oriented vertically). This allows a sufficient quantity of saline to be released upon use without concern that the saline will leak through the adhesive ring. An alternative to solving the same problem is improving the perimeter seal (e.g., by using a wider band of pressure-sensitive adhesive, using an adhesive that is more resistant to leakage of the saline, or using a compressible sealing element).

Various types of absorbent material can be used to contain the electrolyte. In some implementations this material forms a pad such as absorbent pad 40. Preferably, the absorbent materials is able to attract and retain the amounts of electrolytic solution needed for reliable wetting of both the patient surface and the metallic current carrying portion (usually made of tin or silver/silver chloride) of the electrode assembly, allow conduction of sufficient electricity through the thickness of the absorbent material, retain the needed amount of solution for extended periods of time (life of the electrodes), not dissolve in the solution, nor promote precipitation (by providing nucleation sites) within the advertised storage temperature range. There are at least two categories of materials that fulfill these requirements: (1) materials having good capillary action (i.e., materials made from some type of fiber); (2) sponges (i.e., materials made with many small interconnecting channels. In both cases, negative pressure causes electrolytic solution to be drawn into the materials and retained. Some (but by no means all) of the high temperature varieties of category (1) materials include: cotton fiber (cotton batting), ceramic fibers (such as zirconium carbonate or zirconium oxide), cellulose fiber, fiberglass yarns, polyglass yarns, carbon fibers, Aramid, Kelvar, E-glass, Numa, quartz, calcium silicate (and other) insulating materials, paper towel material, industrial wipes, etc. High temperature sponges (category (2) material) may be made from some of the above (such as cellulose or Kelvar) or (more commonly) from industrial plastics. Because of availability, low cost, and ease of automated assembly, cotton batting is a preferred material, although any of the above (and other similar materials) will serve.

The invention is not limited to using saline solution as an electrolyte. Various electrolytes can be used. Electrolytes are often referred to as the entire solution that carries current. In the purest sense, however, the term electrolyte refers to any and all ionic compounds as well as many polar covalent compounds (such as acids) that react with a solvent (almost always the solvent is water) to form ions. An example of the latter is acetic acid—a poor but real, electrolyte since (like many polar compounds) the dissociation of compounds into ions is only partial. Good electrolytes thus encompass any ionic materials (and they include a host of halides, hydroxides, sulfates, etc.) that may dissolve in a solvent (usually, but hardly always, this is water). All electrolytes raise the boiling point and depress the freezing point of solutions by different amounts, sometimes rather dramatically, so that certain compounds such as magnesium sulfate, calcium chloride (and others) can be considered for electrolytic solutions that have to operate well above 400° F. and can still be stored at temperatures well below room temperature without precipitation of a second phase. Thus, almost any ionic compound dissolved in water or a solvent having sufficiently low resistance to ionic diffusion (such as a gel or a semi-solid) will serve as an electrolytic solution and might carry the necessary current for diffusion, corrosion, defibrillation, etc. A simple, easy to make, inexpensive, and good current carrying solution (but by no means the only electrolytic solution of possible use) is saline solution, i.e., sodium chloride dissolved in water.

While the embodiments discussed above include a screen to prevent passage of glass fragments to the patient's skin, the screen can be omitted if desired. For example, if the absorbent pad is constructed to prevent passage of glass fragments, a screen is not necessary.

Further, it is not necessary to encapsulate the electrolyte to practice aspects of the invention that do not require encapsulation, e.g., use of a high temperature adhesive, and use of a pressurized package or cover.

What is claimed is:

1. A medical electrode product comprising:
   (a) an electrode comprising:
      a housing;
      a conductor within the housing; and
      a conductive liquid disposed within a chamber that is constructed to separate the conductive liquid from the conductor until the electrode is to be used; and
   (b) a package, in which said electrode is disposed prior to use, including an actuator device constructed to release said conductive liquid from the chamber when the electrode is removed from the package,
   wherein said actuator device comprises rolls through which the electrode is pulled during removal from the package.

2. The product of claim 1 wherein said chamber comprises a breakable capsule.

3. The product of claim 2 wherein said breakable capsule comprises a glass ampule.

4. The product of claim 1 wherein said rolls are positioned to rupture said chamber during removal.

5. The product of claim 1 wherein said electrode further comprises an absorbent pad, positioned adjacent the conductor on the side of the conductor that is closer to the patient's skin when the electrode is in use.

6. The product of claim 1 wherein said conductor comprises a screen or mesh material.

* * * * *